United States Patent [19]
Fitzpatrick et al.

[11] Patent Number: 5,730,130
[45] Date of Patent: Mar. 24, 1998

[54] LOCALIZATION CAP FOR FIDUCIAL MARKERS

[75] Inventors: J. Michael Fitzpatrick, Nashville, Tenn.; Jennifer J. McCrory, Lincoln, R.I.

[73] Assignee: Johnson & Johnson Professional, Inc., New Brunswick, N.J.

[21] Appl. No.: 459,549

[22] Filed: Jun. 2, 1995

Related U.S. Application Data

[63] Continuation of Ser. No. 162,986, Dec. 8, 1993, abandoned, which is a continuation-in-part of Ser. No. 17,167, Feb. 12, 1993.

[51] Int. Cl.⁶ .................................................. A61B 6/00
[52] U.S. Cl. ................. 128/653.1; 128/654; 128/653.4; 128/898; 606/130
[58] Field of Search ........................... 128/653.1, 653.2, 128/653.4, 653.5, 654, 630, 898; 606/130, 897; 378/204, 205

[56] References Cited

U.S. PATENT DOCUMENTS

| | | | |
|---|---|---|---|
| 3,836,776 | 9/1974 | Gullekson | 250/312 |
| 4,310,507 | 1/1982 | Luckey | 424/4 |
| 4,583,538 | 4/1986 | Onik et al. | 128/303 B |
| 4,608,977 | 9/1986 | Brown | 128/303 B |
| 4,612,930 | 9/1986 | Bremer | 128/303 B |
| 4,615,876 | 10/1986 | Troutner et al. | 424/1.1 |
| 4,615,879 | 10/1986 | Rung et al. | 424/9 |
| 4,618,978 | 10/1986 | Cosman | 378/164 |
| 4,662,887 | 5/1987 | Turner et al. | 623/16 |
| 4,669,481 | 6/1987 | Eisenberg et al. | 128/654 |
| 4,675,173 | 6/1987 | Widder | 424/9 |
| 4,728,575 | 3/1988 | Gamble et al. | 428/402.2 |
| 4,729,892 | 3/1988 | Beall | 424/9 |
| 4,760,173 | 7/1988 | Klaveness | 562/449 |
| 4,860,331 | 8/1989 | Williams et al. | 378/163 |
| 4,927,624 | 5/1990 | Bryant et al. | 424/9 |
| 4,991,579 | 2/1991 | Allen | 128/653 |
| 5,019,370 | 5/1991 | Jay et al. | 424/4 |
| 5,023,072 | 6/1991 | Cheng | 424/9 |
| 5,046,498 | 9/1991 | Fishman | 128/653 |
| 5,055,288 | 10/1991 | Lewis et al. | 424/9 |
| 5,099,846 | 3/1992 | Hardy et al. | 128/653.1 |
| 5,120,527 | 6/1992 | Li et al. | 424/9 |
| 5,138,165 | 8/1992 | Petroff | 250/363.03 |
| 5,142,930 | 9/1992 | Allen et al. | 74/469 |
| 5,197,476 | 3/1993 | Nowacki et al. | 128/660.03 |
| 5,394,457 | 2/1995 | Leibinger et al. | 378/162 |
| 5,397,329 | 3/1995 | Allen | 606/73 |

FOREIGN PATENT DOCUMENTS

| | | |
|---|---|---|
| 0 146 699 | 7/1985 | European Pat. Off. . |
| 0 427 358 | 5/1991 | European Pat. Off. . |
| 0 591 712 | 4/1994 | European Pat. Off. . |

OTHER PUBLICATIONS

Journal of Computer Assisted Tomography, Mar./Apr. 1985, vol. 9, No. 2, 1985, Raven Press, New York, E.E. Babcock: *Edge Artifacts in MR Images: Chemical Shift Effect*.

AJR 154, Jun. 1990, A.S. Smith et al.: *Intracranial Chemical-Shift Artifacts on MR Images of the Brain: Observations and Relation to Sampling Bandwidth*, pp. 1275–1283.

(List continued on next page.)

*Primary Examiner*—Ruth S. Smith
*Attorney, Agent, or Firm*—Kenyon & Kenyon

[57] ABSTRACT

A detachable cap for use in determining the location of the center of the imageable portion of a fiducial marker is disclosed. The lower portion of the cap has three arms and a boss for providing a detachable connection with an implanted base portion to which an imaging marker can be attached. The upper portion of the cap includes a divot—like depression that is configured to mate with a ball whose center can be determined. The ball, marker, and divot are configured so that the center of the ball, when mated to the divot, is coincident with the center of the marker when it is attached to the base in place of the cap. Knowledge of the location of the center of the ball when it is brought into engagement with the divot of the cap can be used to determine the location of the center of the marker when it is attached to the base.

5 Claims, 5 Drawing Sheets

OTHER PUBLICATIONS

AJR, vol. 145, Jul. 1985, J.C. Weinreb et al.: *Chemical Shift Artifact in Clinical Magnetic Resonance Images at 0.35 T*, pp. 183–185.

Radiology, vol. 181, No. 1, Oct. 1991, R.C. Smith et al.: *Chemical Shift Artifact: Dependence on Shape and Orientation of the Lipid–Water Interface*[1], pp. 225–229.

Radiology, vol. 158, No. 2, Feb. 1986: *Pituitary Fossa: Chemical Shift Effect in MR Imaging*[1], pp. 461–462.

Radiology, vol. 153, No. 3, Dec. 1984: *Chemical Shift Misregistration Effect in Magnetic Resonance Imaging*[1], pp. 819–820.

Proceedings of the Meeting of the American Society for Stereotactic and Functional Neurosurgery, Pittsburgh, PA, Jun. 16–19, 1991, Stereotact Funct Neurosurg 1992; 58:103–107, 1992 S. Karger AG, Basel; by R.J. Maciunas et al.: *An Independent Application Accuracy Evaluation of Stereotactic Frame Systems*.

Chapter 14 of *Magnetic Resonance Imaging*, Second Edition, David D. Stark et al., Mosby Publishing, St. Louis, 1992.

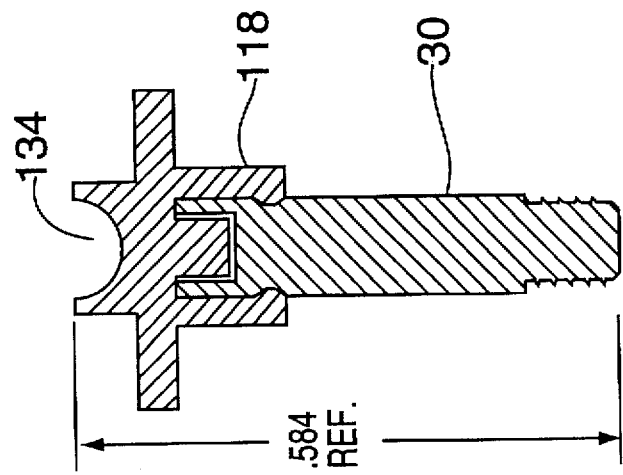
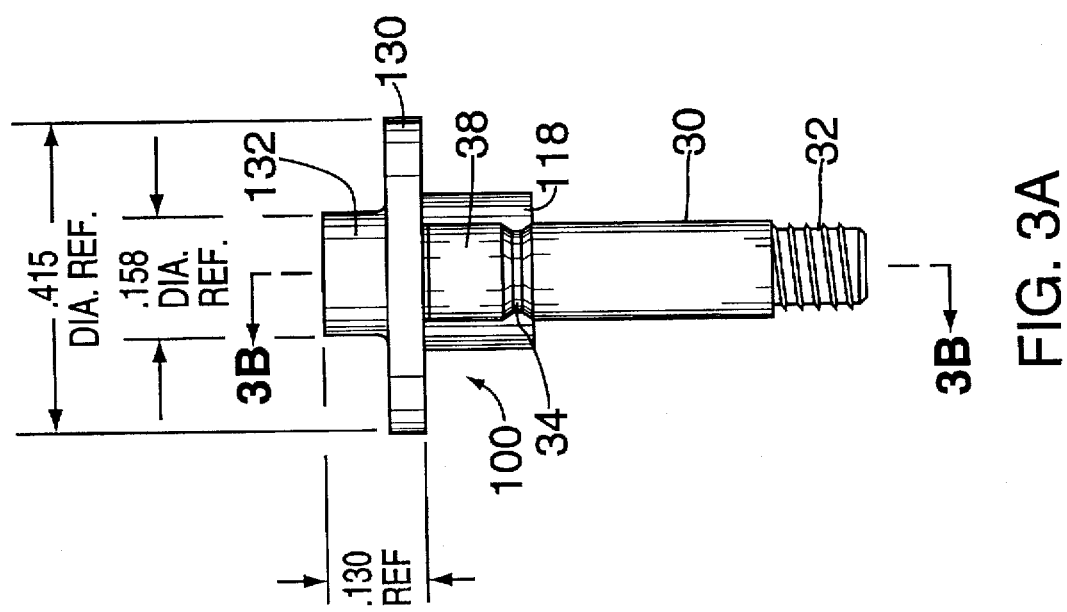
FIG. 3B
FIG. 3A

LOCALIZATION CAP FOR FIDUCIAL MARKERS

This application is a continuation of application Ser. No. 08/162,986, filed 8 Dec., 1993, now abandoned, which is a continuation-in-part of application Ser. No. 08/017,167 filed 12 Feb., 1993.

BACKGROUND OF THE INVENTION

Recent years have seen the development of diagnostic techniques that allow the practicing clinician to obtain high fidelity views of the anatomical structure of the human body. Imaging systems such as computed tomographic (CT) x-ray imagers, positron emission tomographic (PET) scanners, single photon emission computed tomography (SPECT) scanners and nuclear magnetic resonance imaging (MRI) machines have provided clinicians with the ability to improve visualization of the anatomical structure of the human body without surgery or other invasive techniques. In lieu of exploratory surgery, the patient can be scanned by these imaging systems, and the patient's anatomical structure can be reproduced in a form for evaluation by a trained doctor. A problem associated with such scanning techniques concerns the accurate selection and comparison of views of identical areas in images that have been obtained by imagers at different times or by images obtained essentially at the same time using different image modalities, e.g., CT, MRI, SPECT, and PET. This problem has two aspects. First, in order to relate the information in an image of the anatomy to the anatomy itself, it is necessary to establish a one-to-one mapping between points in the image and points of anatomy. This is referred to as registering image space to physical space.

The second aspect concerns the registration of one image space onto another image space. The goal of registering two arbitrarily oriented three dimensional images is to align the coordinate systems of the two images such that any given point in the scanned anatomy is assigned identical addresses in both images. The calculation of the rigid body transformation necessary to register the two coordinate systems requires knowledge of the coordinate vectors of at least three points in the two systems. Such points are called "fiducial points" or "fiducials," and the fiducials used are the geometric centers of markers, which are called "fiducial markers". These fiducials are used to correlate image space to physical space and to correlate one image space to another image space. The fiducial markers provide a constant frame of reference visible in a given imaging mode to make registration possible.

The general technique for using fiducial markers to obtain registration of image data across time is set forth in U.S. Pat. Nos. 4,991,579 and No. 5,142,930, the contents of both of which are incorporated herein by reference. Briefly, these patents teach implanting within a patient a series of three fiducial markers whose location can be determined in the image space of an imager.

Broadly speaking, image markers can be either temporary or permanent with respect to the duration of their placement within the human body. Permanent markers are placed entirely beneath the epidermis of the skin for extended periods of time. Temporary markers (more fully described in the parent application Ser. No. 08/017,167) have two parts: a base that is implanted into bone, and a temporary image marker portion that is attached to the base for brief intervals of time. In the temporary marker, the image marker portion protrudes from the skin.

In both the temporary and the permanent markers, the marker portion may take the form of a hollow container that is charged with aqueous imaging agents to provide imaging capability in the desired imaging modality or modalities. Parent application Ser. No. 08/017,167 (the contents of which are incorporated herein by reference) more fully discusses the structure of each type of marker and the imaging agents which can be used therewith.

Whichever type of marker is employed, its precise location, or more accurately, the precise location of the geometric center of the imageable portion of the marker, must be determined with respect to a defined external coordinate system in physical space. With respect to permanently implanted markers, ultrasound can be used to determine non-invasively the location of the fully implanted marker. Other techniques can be employed with respect to temporary, externally protruding markers. One method involves bringing the tip of an external probe whose location in physical space is known into proximity with the marker itself. However, this may result in significant errors in the location of the precise volumetric centroid of the imaging portion of the marker. There remains a need for a technique for locating the center of a temporary fiducial marker that is simple to practice and which is very accurate.

SUMMARY OF THE INVENTION

In view of the foregoing needs, the present invention provides medical workers with a localization cap that can be detachably mounted to the base portion of a temporary fiducial marker assembly that has been rigidly affixed to bone. The localization cap is provided with a concave depression or divot shaped so that a spherical ball can mate with it in only one position. An intraoperative localization device, which is a wand or probe that terminates in a ball shaped to mate with the divot, is provided to help determine the location of the volumetric center of the imageable portion of the marker relative to the base (when the marker is attached to the base) as follows.

The location of the center of the ball at the end of the probe is defined with respect to physical space by one of a number of known techniques. For example, the probe may be connected to an articulated arm equipped with sensors that measure the orientation of each segment of the arm with respect to its adjacent portion and base as (this technique is more fully discussed in U.S. Pat. No. 5,142,930). Another approach is to utilize a hand-held probe covered with a network of light emitting diodes configured to flash in a pre-determined sequence. A series of several detectors is placed in the operating theater about the probe so that the orientation and location of the probe and spherical probe tip with respect to physical space can be computed by reference to the pattern of flashes emitted from the diodes.

The ball, marker, and localization cap are configured so that the center of the ball, when placed firmly within the divot, will occupy a point in space that corresponds to the volumetric centroid of the imaging portion of the marker when it is attached to the base. Therefore, by labeling the location of the ball of the intraoperative localization device in physical space when it is mated with the divot, one also obtains the location of the exact center of the marker when it, instead of the location cap, is attached to the base.

BRIEF DESCRIPTION OF THE DRAWINGS

For a more complete understanding of this invention, reference should now be made to the embodiments illustrated in greater detail in the accompanying drawings and described below. In the drawings:

FIG. 3A is an elevational view of the fiducial marker assembly, in which the localization cap instead of a marker is shown attached to the base;

FIG. 3B illustrates in cross section the embodiment shown in FIG. 3A as viewed along line A—A;

DETAILED DESCRIPTION

Figure 1B:
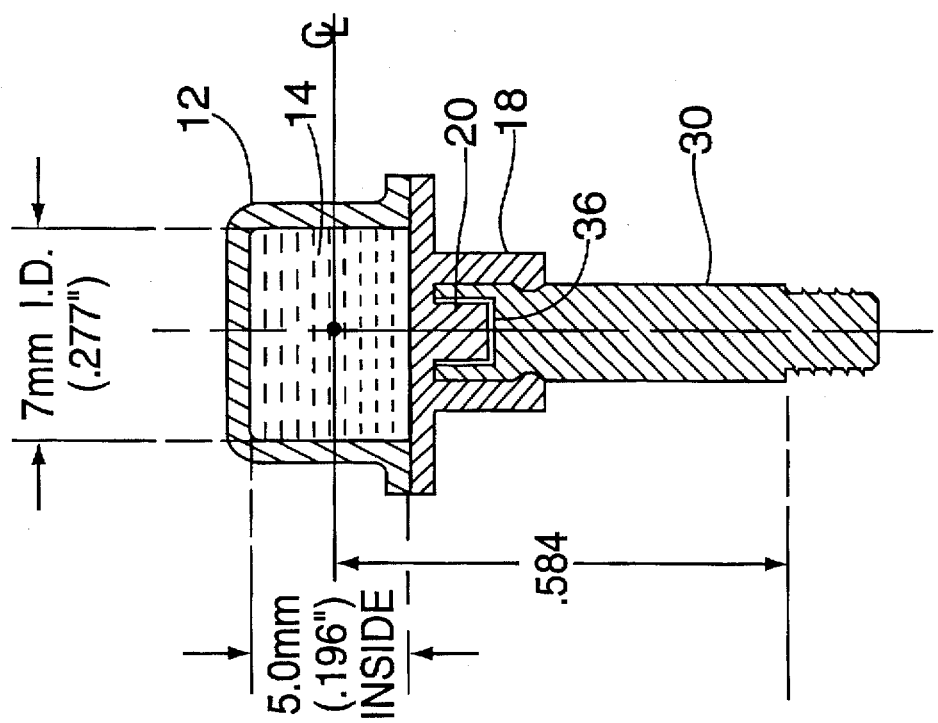
FIG. 1B is a cross-sectional view of the marker and base shown in FIG. 1A as viewed along line A—A.
Figure 1A:
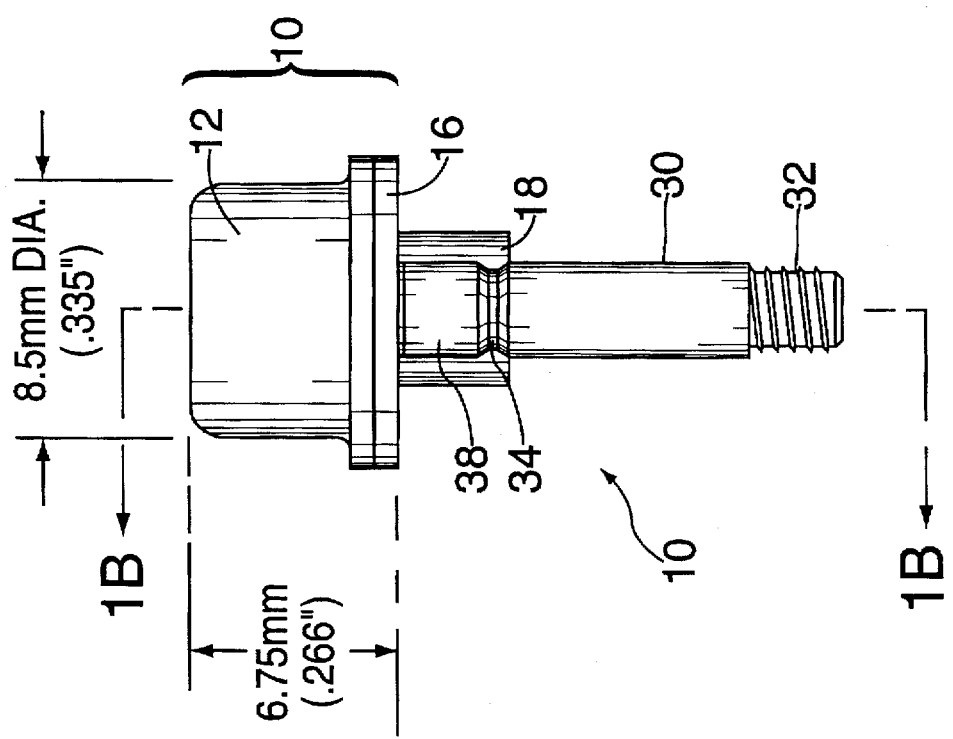
FIG. 1A is an elevational view of a fiducial marker attached to an implantable base.
Figure 2A:
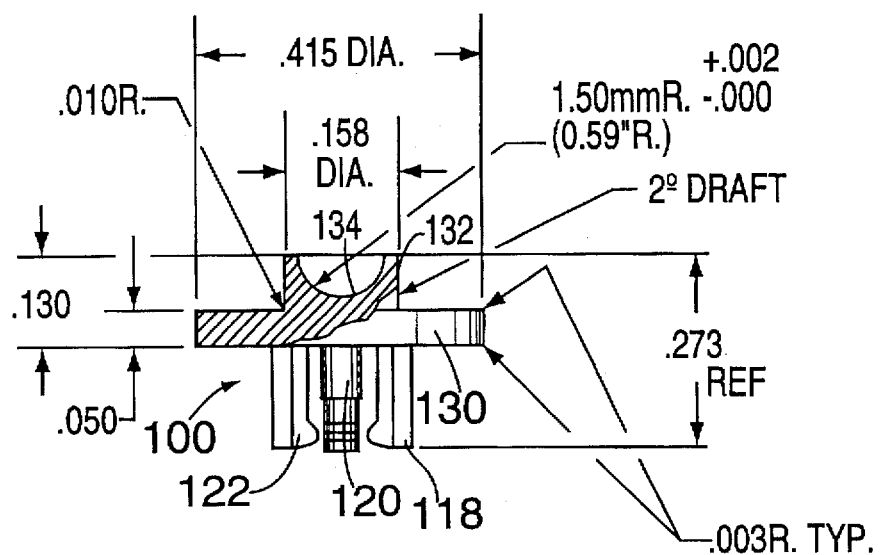
FIG. 2A is an elevational view of the localization cap shown partially in section.
Figure 2B:
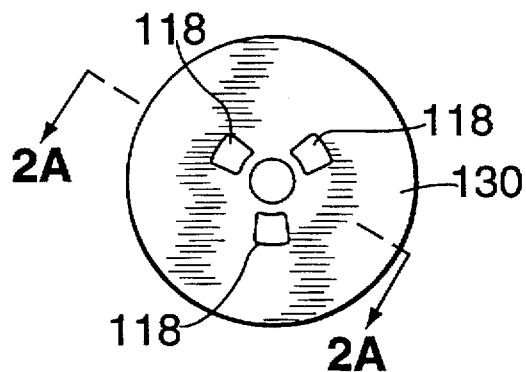
FIG. 2B is a bottom plan view of the localization cap shown in FIG. 2A.
Figure 2C:
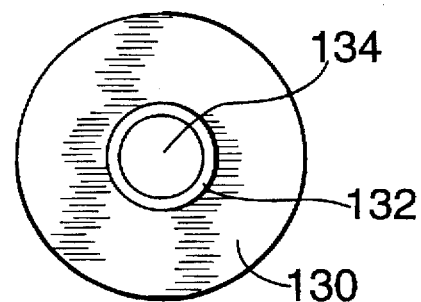
FIG. 2C is a top plan view of the localization cap.

Referring now specifically to the drawings, wherein like numerals indicate like parts throughout, a temporary fiducial marker assembly is indicated in FIGS. 1A and 1B. These figures illustrate a fiducial marker assembly comprising an imaging marker 10 and a base 30. (The dimensions indicated on these and the remainder of the figures are illustrative only, and reflect only one possible embodiment.)

The base 30 has a threaded portion 32 at a first end. The threads enable a surgeon to securely attach the base into the skull or other desired portion of bone tissue. Other connecting structure is provided to securely and releasably link the imaging marker with the base. In the illustrated embodiment, the end of the base opposite the threaded portion terminates in a socket head 38 which contains a socket-like recess 36. (It is anticipated that the base will be implanted into bone with the aid of an insertion tool that twists the base into the bone or into a hole provided in the bone. The recess is non-circular so as to better transmit the torque provided by such an insertion tool.) Just beneath the socket head 38 is a groove 34. As shall be further explained below, the socket 38 and the groove 34 provide for the secure and releasable attachment of both an imaging marker and a localization cap to the base.

The imaging marker portion of the temporary fiducial marker assembly may consist of two principal portions, a cylinder 12 and a cap 16. The cylinder 12 contains a cavity 14 for receiving a mixture of imaging agents whose composition is determined by the imaging modalities to be employed. (For a further discussion of the imaging agents employed, reference is made to the parent application.) While in the illustrated embodiment, the vessel containing the imaging agents is preferably cylindrical, other shapes (such as a prism or sphere) could be employed as well. The cylinder 12 is closed at one end and open at the other to allow for the introduction of the imaging agents. In one version of the device, a cap 16 is used to seal off the open end of the cylinder once the imaging agents have been added to the cylinder. In this version, the cap may be cemented or welded into place.

The imaging marker typically is provided with a protruding boss 20 and a plurality (here, three) of snap arms 18, which terminate with inwardly projecting portions. The shape and dimensions of the boss are in direct correspondence with the shape and size of the socket 36 provided in the base 30 so as to properly and securely center the imaging marker on the base. The snap arms 18 cooperate with the grooves 34 of the base 30 so as to detachably secure the imaging marker onto the base. The cooperation of these elements is illustrated in FIGS. 1A and 1B.

The other component attachable to the base is the localization cap 100. The localization cap can be made of the same polymer as the marker 12, or any other material capable of being formed into a dimensionally stable shape (e.g., metal). Any conventional process for forming precision parts can be employed to form the cap. For example, when a polymer is used, the cap can be formed via injection molding alone or in combination with machining. The localization cap shown in FIGS. 2A–3B has a divot 134 formed into a divot socket 132. The divot is sized and shaped with respect to the localization cap and the imaging marker so that when the localization cap is placed on the base 30, its center of curvature is coincident with the geometric center of the fluid-filled cavity of the marker 12 when the latter is attached to the base 30.

Similar to the marker 12, the localization cap is provided with a protruding boss 120, and a trio of snap arms 118 terminating with inwardly projecting tips 122. The shape and dimensions of the boss are again in direct correspondence with the shape and size of the socket 36 provided in the base 30 so as to properly and securely center the localization cap to the base. The snap arms 118 cooperate with the groove 34 of the base 30 so as to detachably secure the localization cap onto the base.

Figure 4:
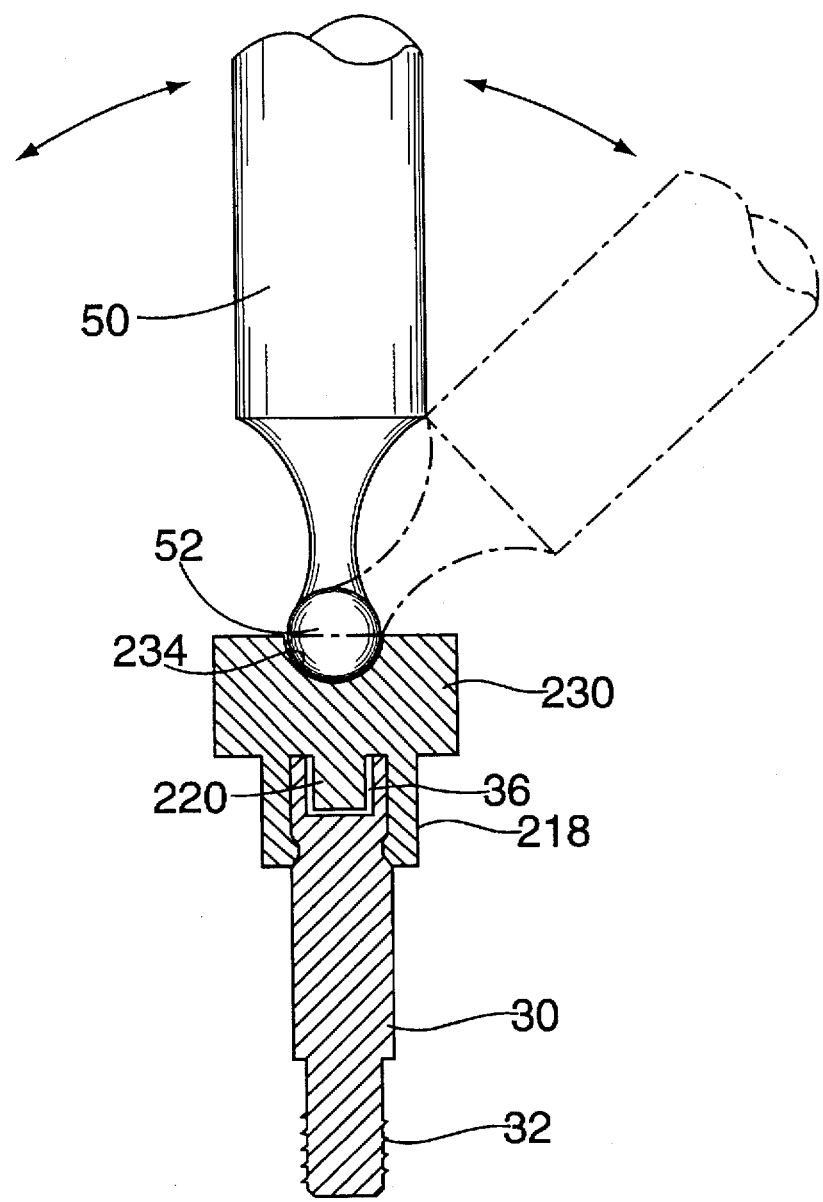
FIG. 4 is a sectional view of a second embodiment of the localization cap attached to its base, in cooperation with an intraoperative localization device.

FIG. 4 illustrates another embodiment of the localization cap having a divot 234, which also employs a boss 220 and snap arms 218 to effect connection to the base 30. This localization cap differs from the previous embodiment in that it lacks a skirt 130 and utilizes a thicker divot socket 230. While these embodiments utilize snap arms to connect the localization cap to the base, other fastener structure may be provided for attaching the localization cap to the base, such as screw threads, clasps, hooks, etc.

In the embodiments of the localization cap shown in FIGS. 2–5A, the divot is seen to take the form of a hemisphere that mates with a ball. However, other shapes can be used. For example, in FIG. 5B, the divot takes the form of a cylinder 334; in FIG. 5C, the divot takes the form of a conical section 434. Any divot shape that provides a fixed mating surface for the tip of the localization device can be employed, and these illustrated shapes are merely examples of several such possible divot shapes. While the ball at the end of the probe could similarly be replaced with a tip having a different shape (such as a conical projection or a prism), a spherical ball is preferred, as it allows the greatest variation in the orientation of the probe while it remains mated to the divot.

The method of utilizing the localization cap shall now be explained in detail in the context of neurosurgery. A series of at least three (and preferably four) bases is inserted into a corresponding number of holes drilled in the skull. A temporary marker is attached to each of these bases, and the patient is then subjected to one or more scans in the radiological suite. The markers are designed to be visible in the image space of each scan taken, so that their geometric centers can be localized and used to define a series of points sufficient to form the basis of an addressable internal coordinate system with respect to the image space.

After the scans have been taken, the markers are detached from their respective bases. At this point, the patient typically will be removed from the radiology suite, as the surgeon studies the scans to plan a subsequent surgical procedure or radiological treatment.

After the surgical procedure to be performed on the patient is decided upon, the patient is transported to the operating theater and immobilized in a skull clamp. The skull clamp serves to force the head of the patient into a more or less fixed relationship with respect to his external physical environment. However, the skull clamp does not itself make known the mathematical relationship that exists between the internal coordinate system previously established by the temporary markers and the external environment in which the surgeon operates. In order for the surgeon to determine the relationship between physical space (e.g., the operating room at the time of surgery) and the image space with respect to which the image data has been defined, the localization caps are employed.

Figure 5A:
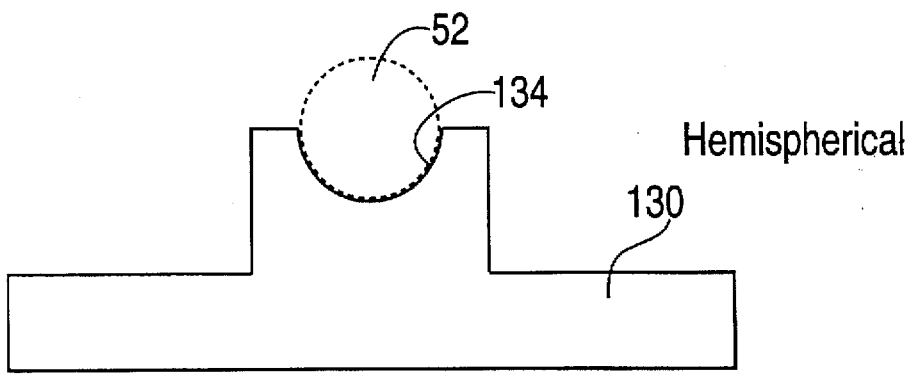
FIG. 5A shows the manner in which the ball (shown in phantom) mates with a hemispherical depression in a localization cap.
Figure 5B:
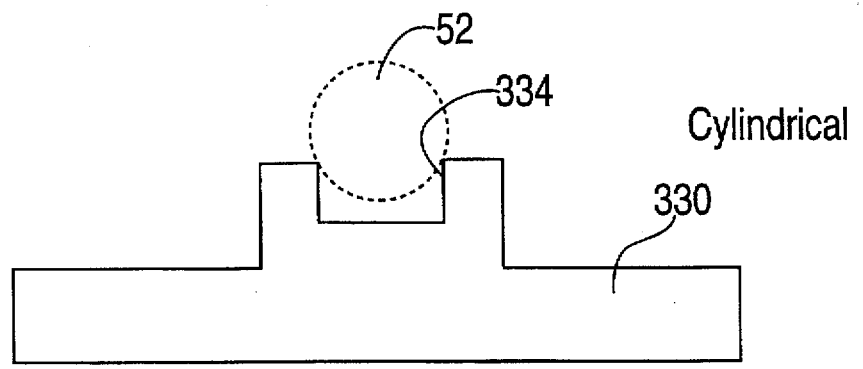
FIG. 5B shows the manner in which the ball (shown in phantom) mates with a cylindrical depression in a localization cap.
Figure 5C:
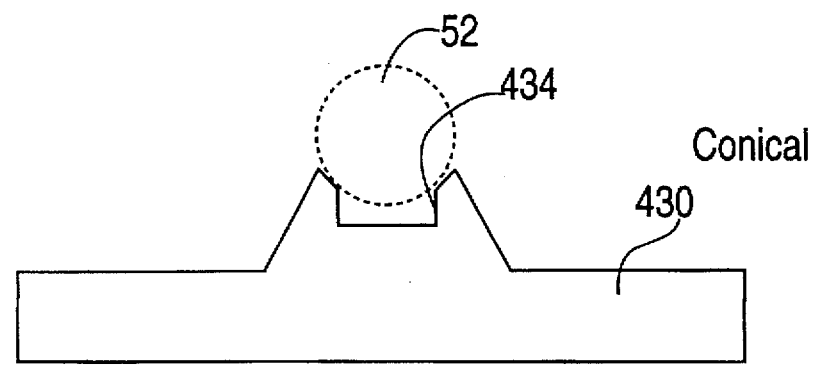
FIG. 5C shows the manner in which the ball (shown in phantom) mates with a conical depression in a localization cap.

The surgeon snaps the localization caps into place on the marker bases. The surgeon then brings the ball 52 of the probe 50 into cooperative engagement with the divot 234 (FIG. 4), which may be hemispherical (FIG. 5A), cylindrical (FIG. 5B), or conical (FIG. 5C). At this point, the center of the ball 52 is coincident with a point in space that corresponds to the centroid of the imaging portion of the marker 12 when the latter is affixed to the base 30. Any means for defining the location in physical space of the center of the ball 52 can be used to provide the corresponding physical space address of the centroid of the imaging marker previously located in image space. In other words, an address in image space (the centroid of a marker) is related to physical space. By providing three linearly independent such addresses—i.e., the addresses of the three centroids of the three markers—every address in image space can be assigned a discrete address in physical space, and every address in physical space can be related back to an address in image space.

One method of so defining the location of a point in space is set forth in U.S. Pat. No. 5,142,930. In this patent, the probe is located at the end of an articulated arm whose orientation in space is monitored by a computer. The computer senses the angular orientation of each segment of the articulated arm. By using arm segments of fixed length, this information can be used to define the location of the ball at the end of a probe attached to or integrated with the arm in physical space.

One disadvantage of using an articulated arm is its size. The arm may take up space that the surgeon would prefer be utilized in another manner. Also, because of its size, the arm may be cumbersome to manipulate. Another technique for defining the location of the center of the ball 52 that lacks these shortcomings utilizes a freely moveable hand-held wand terminating in the ball 52. The wand is provided with a number of flashing light emitting diodes. The light given off by the LEDs is detected by a series of several detectors that provide information regarding the position of the LEDs to a computer. The computer uses this information to compute the position and orientation in physical space of the wand, including the particular address of the center of the ball 52 at its tip. The surgeon firmly places the ball of the wand into the divot of the localization cap and then presses a button on the wand which signals to the computer that the ball is centered at the address which corresponds to the corresponding marker centroid. (A fuller description of such a system is provided in U.S. Pat. No. 5,197,476, the contents of which are herein incorporated by reference.) This is repeated for each localization cap, which then defines the relationship between image space and the physical space occupied by the head of the patient as it lies fixed within the skull clamp in the operating room.

Whichever the technique employed, once the intraoperative localization device has made contact with the localization caps so as to relate image space with physical space, the intraoperative localization device can be used to summon up a broad range of desired images by its further movement. For example, the system can, by continuing to monitor the position of the tip of the intraoperative localization device, be programmed to display images from image space of the corresponding region of the anatomy lying at, adjacent to, or in advance of the tip of the intraoperative localization device. With respect to this last feature, by using the system to determine the trajectory that the tip of the intraoperative localization device follows, one defines a direction of interest to the surgeon. This directional information can be used to provide a so-called "pilot's eye view" of the anatomical region of interest, in which the surgeon sees a display of the region of anatomy that he is about to cut into.

The intraoperative localization device discussed above is specialized solely for the task of providing an address in physical space that can be used to summon up images based on known related addresses in image space. The intraoperative localization device may also be provided in the form of a compound tool capable of performing both as an intraoperative localization device and as a knife or any other conventional tool.

What is claimed is:

1. A kit for determining the center of a fiducial marker, comprising:

a localization cap having an upper surface, a lower surface, and a mating portion located on the upper surface;

a base to which the localization cap can be detachably mounted, said base being configured for attachment to bone tissue;

means located on the localization cap for detachably connecting the localization cap to the base in a manner that does not disturb the location of the base when it is attached to tissue; and a localization probe having an end that terminates in a mating portion that is configured to mate with the mating portion of the localization cap.

2. The kit of claim 1, wherein the mating portion of the localization probe and the mating portion of the localization cap are configured so that when they are in operative engagement with one another, the geometric center of the mating portion of the probe is at a known fixed position relative to the base.

3. A kit for facilitating the establishment of at least one coordinate point with respect to the anatomy of a subject, comprising:

a localization cap having an upper surface and a lower surface and a mating area located on the upper surface;

a localization probe having an end that terminates in a mating portion that is configured to mate with the mating portion of the localization cap;

a base to which the localization cap can be detachably mounted, said base being configured for attachment to bone tissue; and a fiducial marker that can be detachably mounted to the base, said fiducial marker having an imageable portion that has a center, wherein the center of the imageable portion of the fiducial marker, when attached to the base, is coincident with the geometric center of the mating portion of the localization probe when the localization cap is attached to the base and the localization probe is brought into operative engagement with the localization cap.

4. A method for ascertaining the geometric center of a fiducial marker having an imageable portion that can be detachably mounted to a base portion, the method comprising:

attaching to the base a localization cap having a socket shaped so that a sphere can mate with it so as to uniquely define the location of the center of the sphere;

bringing the tip of a probe that terminates in a spherical portion into engagement with the socket; and determining the location of the center of the spherical tip of the probe with respect to a coordinate system.

5. The method of claim 4, wherein the shape of the localization cap is selected so that the location of the center of the spherical tip of the probe when mated to the socket of the localization cap is at the same point relative to the base as the center of the imageable portion of the marker when it is attached to the base, so that by knowing the location in space of the center of the spherical tip of the probe when it is mated to the socket of the localization cap, the location of the center of the marker, when attached to the base, can be determined.

* * * * *